US012599904B2

(12) United States Patent
Chen et al.

(10) Patent No.: US 12,599,904 B2
(45) Date of Patent: Apr. 14, 2026

(54) PRESSURE GENERATING DEVICE AND DETECTING SYSTEM INCLUDING THE SAME

(71) Applicant: Inti Taiwan, Inc., Zhubei City (TW)

(72) Inventors: Wei-Ming Chen, Zhubei City (TW); Ching-Yi Mao, Zhubei City (TW)

(73) Assignee: INTI TAIWAN, INC., Zhubei City (TW)

( * ) Notice: Subject to any disclaimer, the term of this patent is extended or adjusted under 35 U.S.C. 154(b) by 542 days.

(21) Appl. No.: 18/305,966

(22) Filed: Apr. 24, 2023

(65) Prior Publication Data

US 2024/0351035 A1     Oct. 24, 2024

(51) Int. Cl.
B01L 3/00 (2006.01)
B01L 3/02 (2006.01)
G01N 33/50 (2006.01)

(52) U.S. Cl.
CPC ....... B01L 3/502761 (2013.01); B01L 3/0265 (2013.01); G01N 33/5091 (2013.01); *B01L 2200/0647* (2013.01); *B01L 2300/0654* (2013.01); *B01L 2400/0487* (2013.01); *B01L 2400/0633* (2013.01)

(58) Field of Classification Search
CPC ............ B01L 2400/0487; B01L 3/0227; F04B 43/043
See application file for complete search history.

(56) References Cited

U.S. PATENT DOCUMENTS

| | | | | |
|---|---|---|---|---|
| 2007/0172388 A1* | 7/2007 | Padmanabhan | ...... | G01N 29/032 |
| | | | | 422/400 |
| 2007/0243523 A1* | 10/2007 | Ionescu-Zanetti | ......... | |
| | | | | G01N 15/1459 |
| | | | | 977/924 |
| 2009/0165876 A1* | 7/2009 | Atkin | .................. | B01L 3/50273 |
| | | | | 137/833 |
| 2014/0087412 A1* | 3/2014 | Fouras | ................... | G01N 11/00 |
| | | | | 435/287.1 |
| 2018/0066643 A1* | 3/2018 | Chen | ..................... | F04B 17/003 |
| 2023/0383240 A1* | 11/2023 | Takeda | ............... | G01N 15/1434 |

* cited by examiner

*Primary Examiner* — Jonathan M Hurst
(74) *Attorney, Agent, or Firm* — HSML P.C.

(57) ABSTRACT

A pressure generating device includes a tank, a deformable membrane, a driving device, and an actuating arm. The tank defines a chamber therein, and includes an opening and a communication port each of which is in fluid communication with the chamber. The deformable membrane is disposed to seal the opening, and is deformable between a flat state and a deformed state. The actuating arm is coupled to be driven by the driving device to move between a first position, where the deformable membrane is in the flat state, and a second position, where the deformable membrane is forced to be in the deformed state, such that a predetermined negative pressure is generated through the communication port when the actuating arm is driven from one of the first and second positions to the other one of the first and second positions.

14 Claims, 11 Drawing Sheets

PRESSURE GENERATING DEVICE AND DETECTING SYSTEM INCLUDING THE SAME

FIELD

The disclosure relates to a pressure generating device, and more particularly to a pressure generating device and a detecting system including the same for detecting quality of an oocyte or an embryo.

BACKGROUND

In vitro fertilization (IVF) is an option for achieving pregnancy for couples suffering from infertility. In an IVF cycle, after stimulation of the ovaries of the mother using follicle stimulating hormone, several oocytes can be harvested from the ovaries and fertilized in vitro, and then one or more of the fertilized oocytes may be transferred back to the mother. In some cases, the fertilized oocytes may be further developed into embryos in vitro, and then one or more of the embryos are transferred back to the mother. To increase the live-birth rate for an IVF cycle, there is a need to select the fertilized oocytes or the embryos with better quality to be transferred back to the mother.

SUMMARY

Therefore, an object of the disclosure is to provide a pressure generating device and a detecting system including the pressure generating device that can be used for determining quality of an oocyte or an embryo.

According to a first aspect of the disclosure, a pressure generating device includes a tank, a deformable membrane, a driving device, and an actuating arm. The tank defines a chamber therein, and includes an opening and a communication port each of which is in fluid communication with the chamber. The deformable membrane is disposed to seal the opening, and is deformable between a flat state and a deformed state. The driving device is disposed on an outer surface of the tank. The actuating arm is coupled to be driven by the driving device to move between a first position, where the deformable membrane is in the flat state, and a second position, where the deformable membrane is forced to be in the deformed state, such that a predetermined pressure is generated through the communication port when the actuating arm is driven from one of the first and second positions to the other one of the first and second positions.

According to a second aspect of the disclosure, a detecting system is provided for detecting quality of a test sample including an oocyte or an embryo. The detecting system includes the pressure generating device, a micropipette for sucking the test sample, and a connecting tube disposed to connect the communication port of the tank to the micropipette for applying the predetermined pressure to the test sample.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
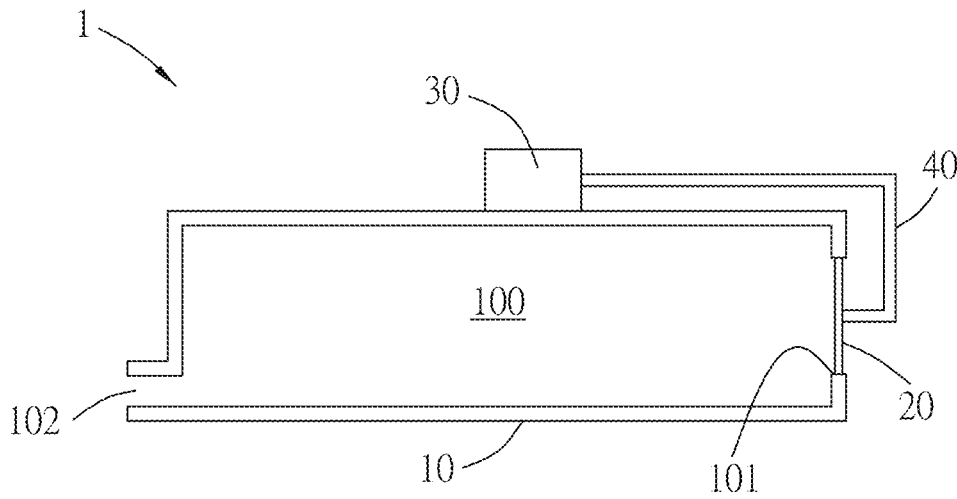
FIG. 1 is a schematic view illustrating a pressure generating device according to a first embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

It should be noted that the drawings, which are for illustrative purposes only, are not drawn to scale, and are not intended to represent the actual sizes or actual relative sizes of the components of the device or the system in this disclosure.

Figure 2:
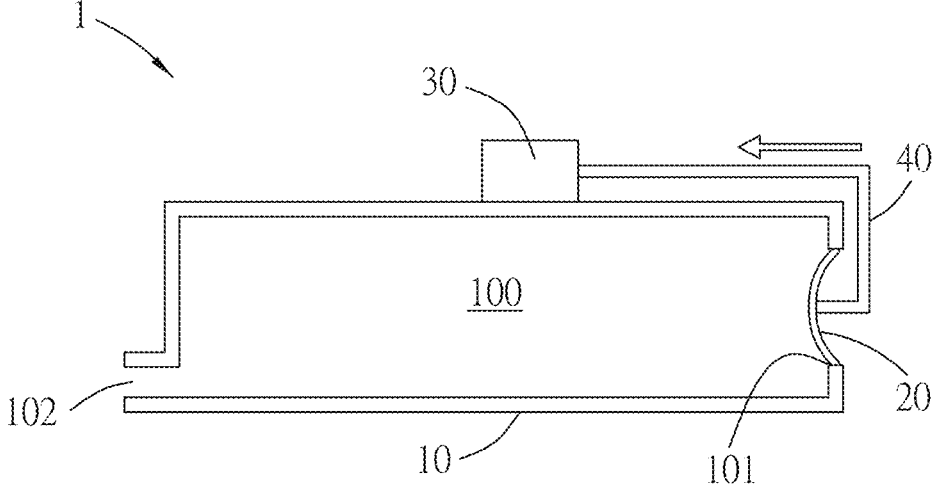
FIG. 2 is a schematic view similar to FIG. 1 but in a pressure increasing state.
Figure 11:
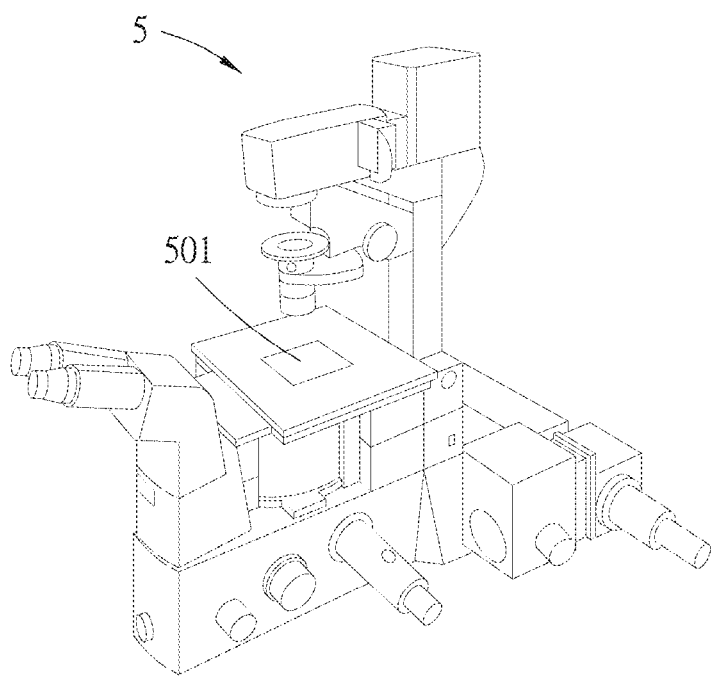
FIG. 11 is a schematic view illustrating a microscope of the detecting system according to an embodiment of the disclosure.
Figure 13:
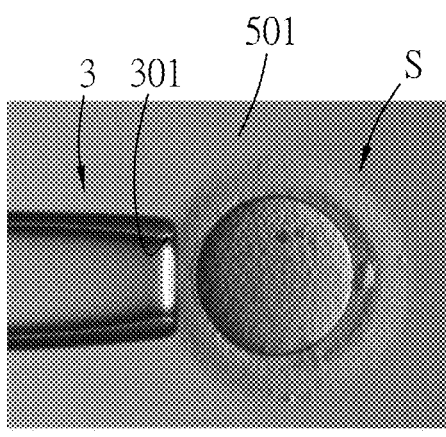
FIGS. 13 and 14 are two microscope images respectively illustrating two states of an oocyte before and after a predetermined negative pressure is provided by the pressure generating device of the detecting system.
Figure 14:
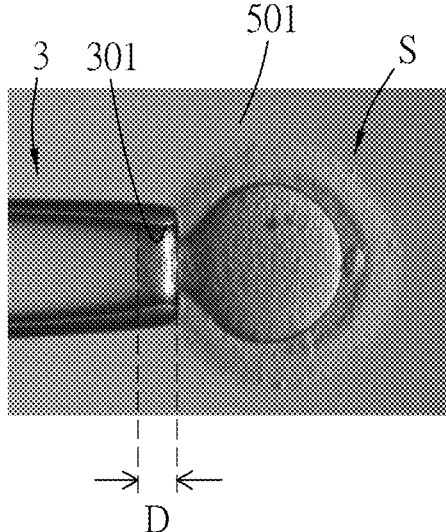

FIGS. 1 and 2 each shows a pressure generating device 1 according to a first embodiment of the disclosure. The pressure generating device 1 is used for generating a pressure to a test sample (S) through a micropipette 3 (see FIGS. 13 and 14). The test sample (S) may be an oocyte (e.g., a mammalian oocyte which may be fertilized or unfertilized) or an embryo (e.g., a mammalian embryo). Based on an aspiration depth (D) of the test sample (S) (see FIG. 14) and other factors (such as morphologies observed using a microscope 5 shown in FIG. 11), the quality of the test sample can be determined.

The pressure generating device 1 includes a tank 10, a deformable membrane 20, a driving device 30, and an actuating arm 40.

The tank 10 defines a chamber 100 therein, and includes an opening 101 and a communication port 102 each of which is in fluid communication with the chamber 100. The deformable membrane 20 is disposed to seal the opening 101, and is deformable between a flat state and a deformed state. The driving device 30 is disposed on an outer surface of the tank 10. The actuating arm 40 is coupled to be driven by the driving device 30 to move between a first position and a second position. In the first position, as shown in FIG. 1, the deformable membrane 20 is in the flat state, while in the second position, as shown in FIG. 2, the deformable membrane 20 is forced to be in the deformed state. When the actuating arm 40 is driven from one of the first and second positions to the other one of the first and second positions, a predetermined pressure is generated through the communication port 102.

In the first embodiment, in response to movement of the actuating arm 40 from the first position (see FIG. 1) to the second position (see FIG. 2), the deformable membrane 20 is forced by the actuating arm 40 to be deformed inwardly so as to convert the deformable membrane 20 from the flat state into the deformed state. With the deformation of the deformable membrane 20, the chamber 100 is converted into a pressure increasing state. In this case, once the deformable membrane 20 returns back to the flat state from the deformed state, the predetermined pressure can be generated from the communication port 102.

In some embodiments, the tank 10 may be made of metals, alloys, plastics, other suitable air-impermeable rigid materials, or combinations thereof. In some embodiments, the deformable membrane 20 may be made of silicone, polymer, fabric, any suitable air-impermeable flexible materials, or combinations thereof.

Figure 3:
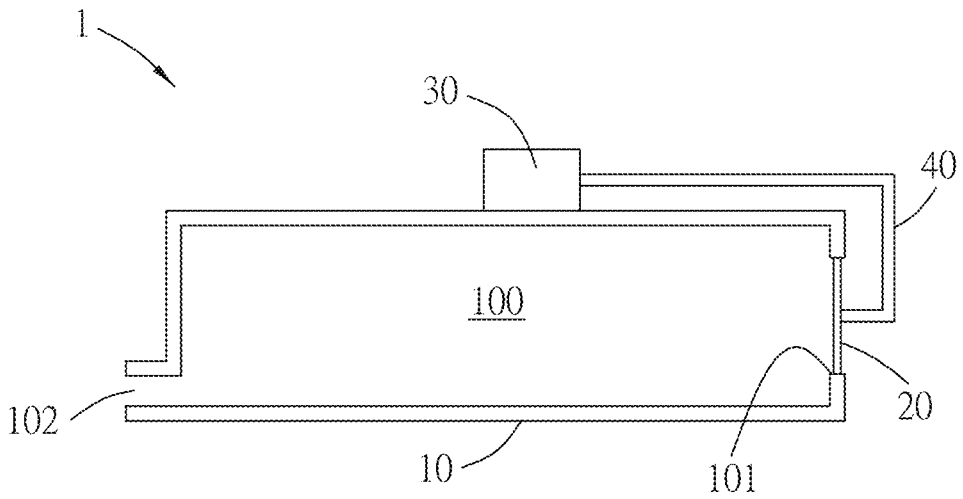
FIG. 3 is a schematic view illustrating a pressure generating device according to a second embodiment of the disclosure.
Figure 4:
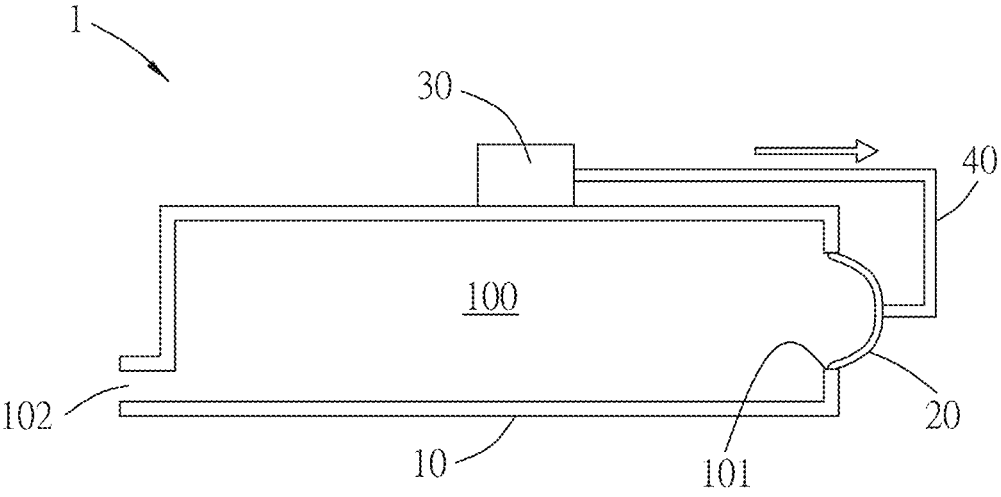
FIG. 4 is schematic view similar to FIG. 3 but in a pressure decreasing state.

FIGS. 3 and 4 illustrate a pressure generating device 1 according to a second embodiment of the disclosure. The second embodiment is similar to the first embodiment, except that in the second embodiment, the deformable membrane 20 is deformed outwardly when in the deformed state. To be specific, in the second embodiment, an end of the actuating arm 40, which is distal from the driving device 30, is secured to the deformable membrane 20. When the actuating arm 40 is in the first position, the deformable membrane 20 can be kept at the flat state. In response to movement of the actuating arm 40 to the second position (see FIG. 4) from the first position (see FIG. 3), the deformable membrane 20 is pulled by the actuating arm 40 to be deformed outwardly so as to convert the deformable membrane 20 from the flat state into the deformed state. With the deformation of the deformable membrane 20, the chamber 100 is converted into a pressure reducing state, and thus the predetermined pressure can be generated from the communication port 102.

FIGS. 5 to 9 illustrate a pressure generating device 1 according to a third embodiment of the disclosure. The third embodiment is similar to the first embodiment, except that in the third embodiment, the tank 10 is shown in detail, and the pressure generating device 1 further includes a slider 50 for coupling the driving device 30 to the actuating arm 40.

Figure 5:
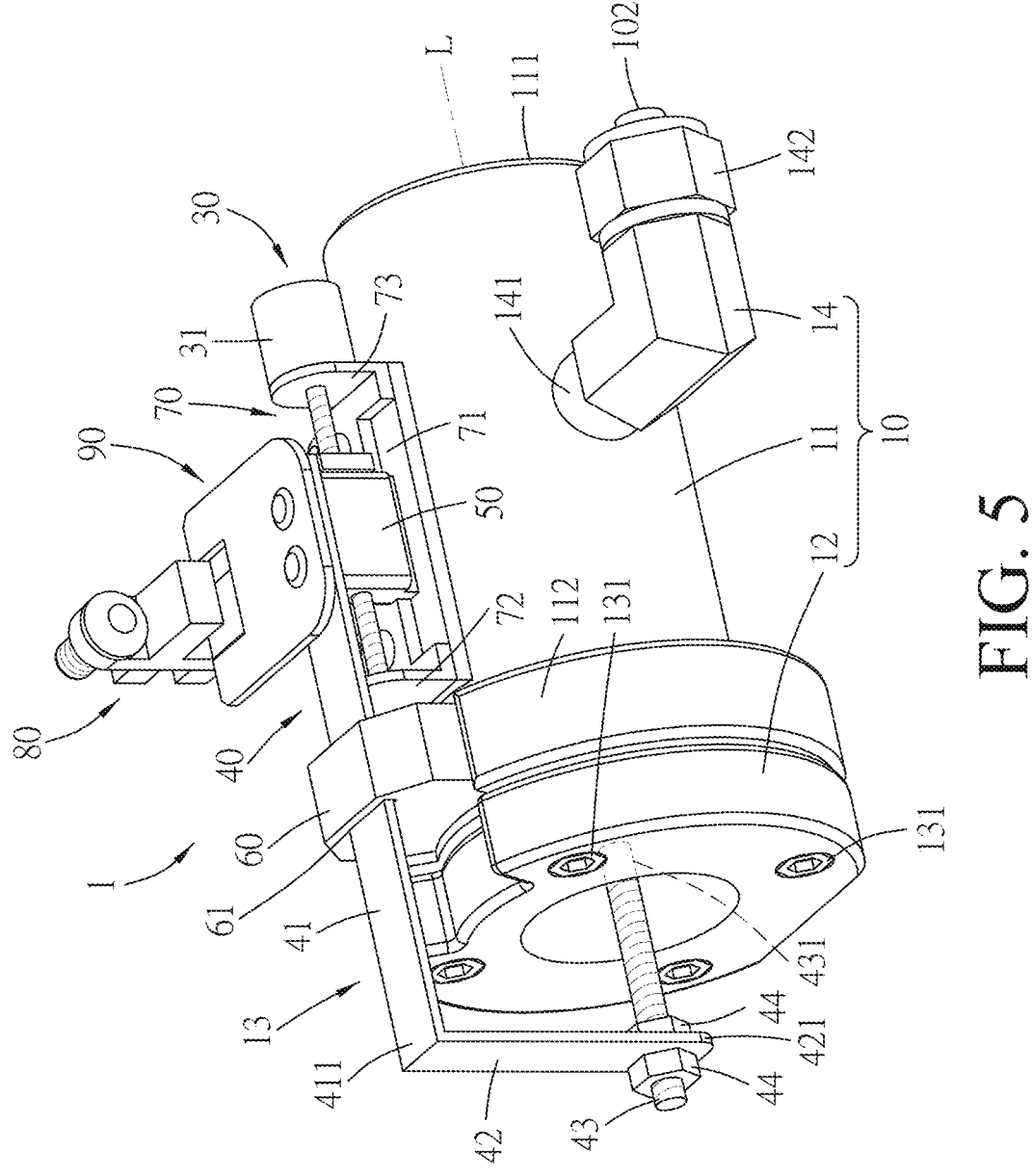
FIG. 5 is a perspective view illustrating a pressure generating device according to a third embodiment of the disclosure.
Figure 6:
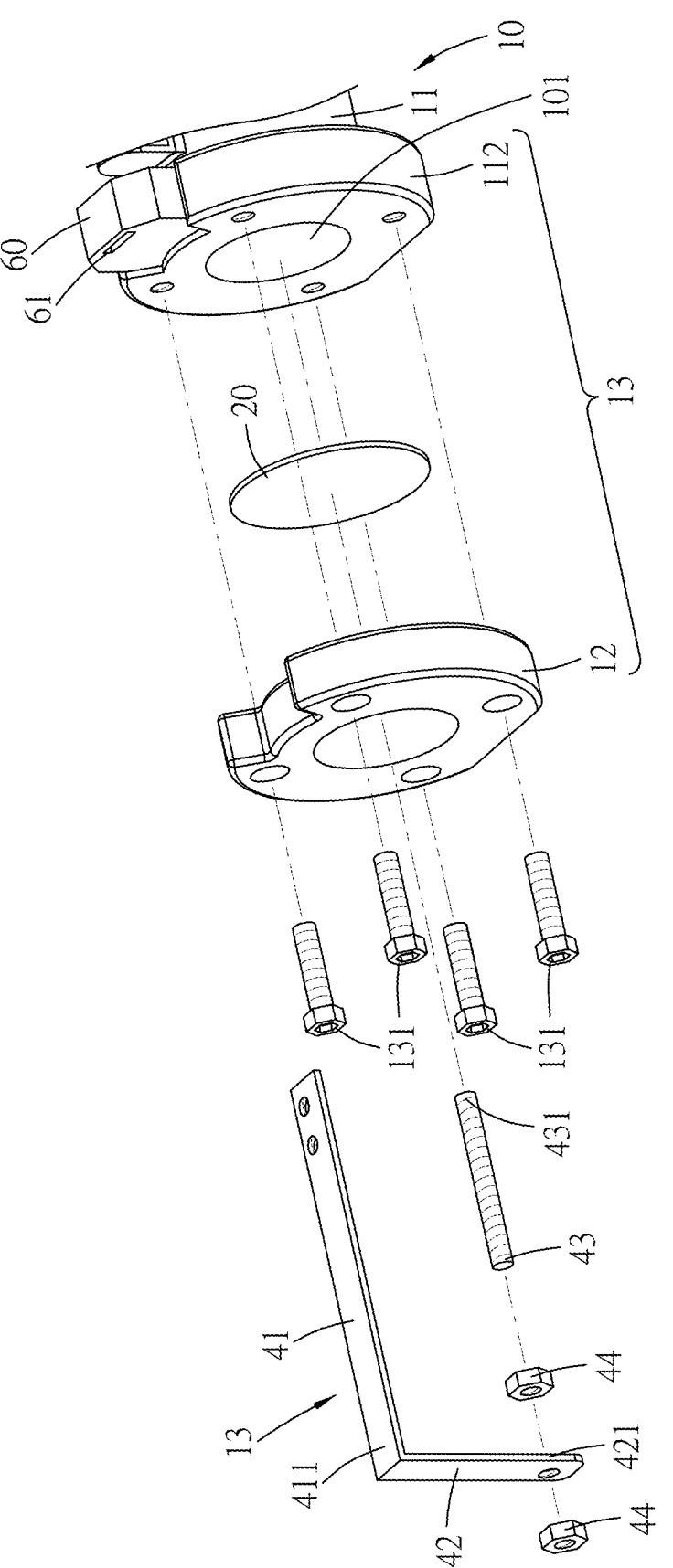
FIG. 6 is a fragmentary exploded perspective view of a tank shown in FIG. 5.
Figure 9:
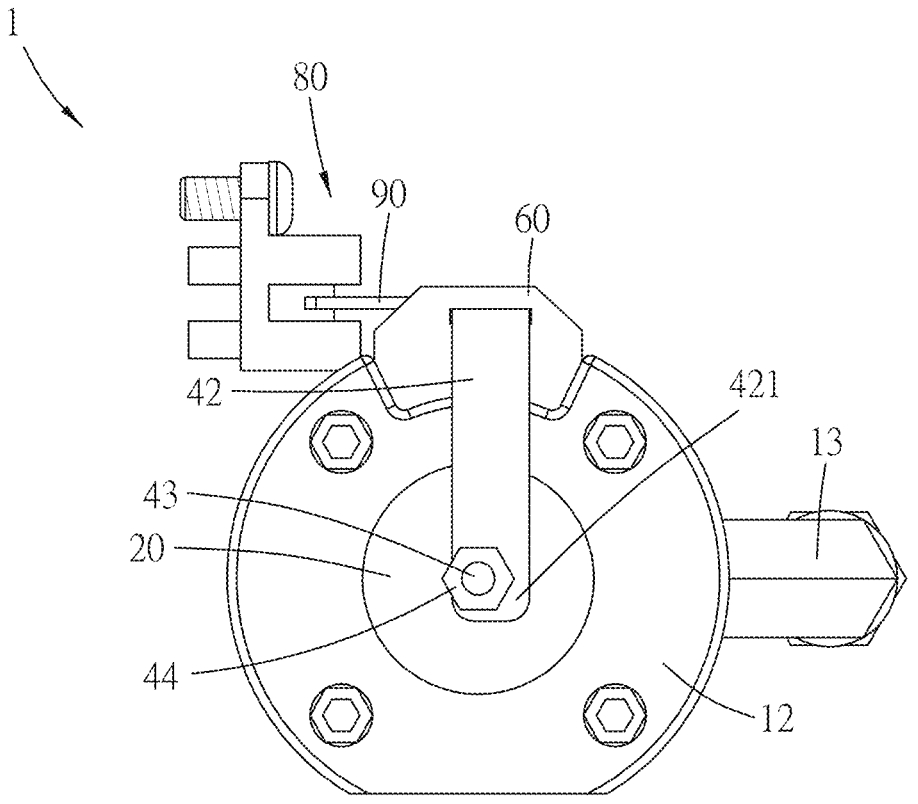
FIG. 9 is a front side view of the pressure generating device shown in FIG. 5.

As shown in FIGS. 5 and 6, the tank 10 includes a surrounding wall 11, a surrounding mount 12 and a connection stem 14. The surrounding wall 11 defines the chamber 100 (see FIGS. 1 and 2) therein, and extends along a longitudinal axis (L) to terminate at a closed end 111 and an enlarged end 112. The enlarged end 112 is disposed opposite to the closed end 111, and is formed with the opening 101. The surrounding mount 12 is detachably mounted to the enlarged end 112 such that the deformable membrane 20 is secured between the enlarged end 112 and the surrounding mount 12 to thereby seal the opening 101. In addition, as shown in FIGS. 5, 6 and 9, a central portion of the deformable membrane 20 is exposed from the surrounding mount 12 when the surrounding mount 12 is mounted to the enlarged end 112. The connection stem 14 includes a first connection end 141 and a second connection end 142. The first connection end 141 is connected to the surrounding wall 11. The second connection end 142 is disposed opposite to the first connection end 141, and defines the communication port 102 which is in fluid communication with the chamber 100 through the connection stem 14.

In some embodiments, the surrounding mount 12 is mounted to the enlarged end 112 through a plurality of fastening elements 131, for example, screws or the like. Other suitable techniques may be used for detachably mounting the surrounding mount 12 to the enlarged end 112. In some embodiments, an end portion 13 of the tank 10, in which the opening 101 is formed, refers to a combination of the surrounding mount 12 and the enlarged end 112, and the deformable membrane 20 is retained in the flat state by the end portion 13 of the tank 10.

Figure 7:
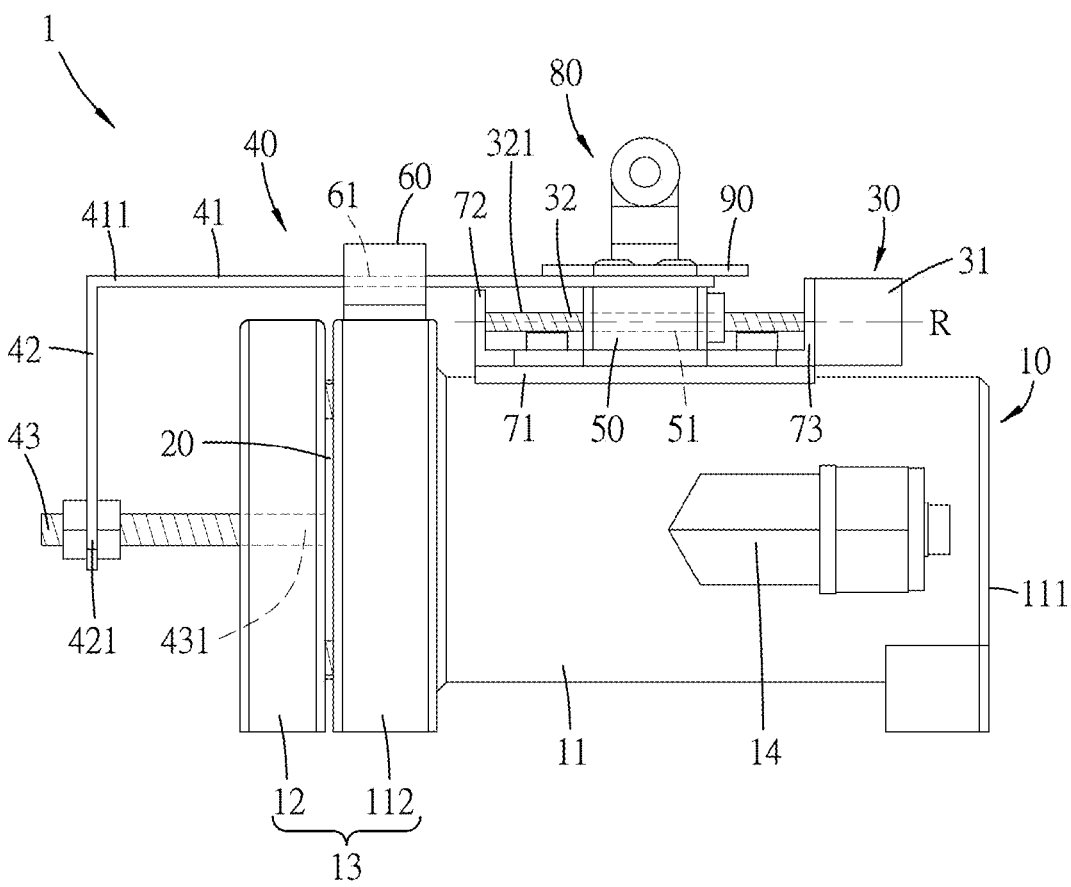
FIG. 7 is a lateral side view of the pressure generating device shown in FIG. 5.
Figure 8:
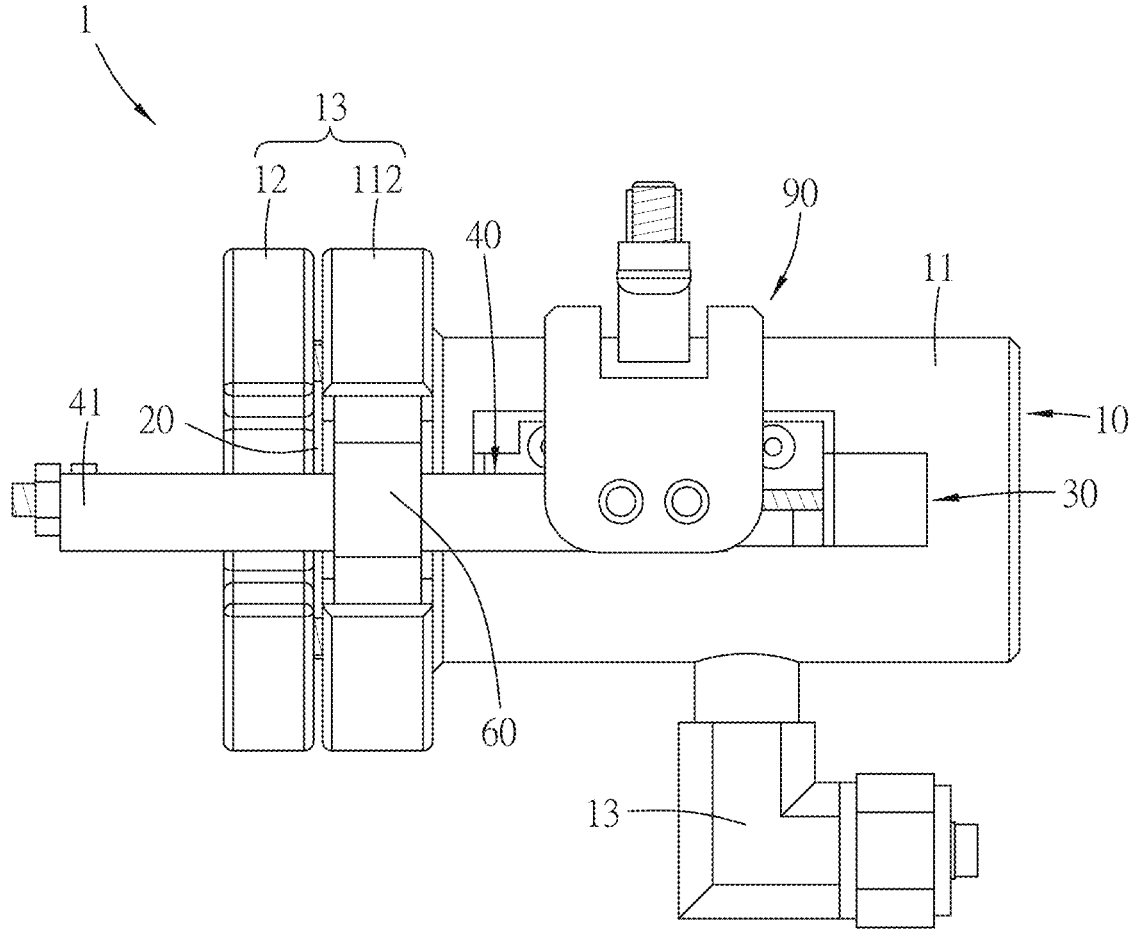
FIG. 8 is a top side view of the pressure generating device shown in FIG. 5.

In some embodiments, as shown in FIG. 7, the driving device 30 is a motor which includes a motor body 31 and an output shaft 32. The motor body 31 is mounted on the outer surface of the tank 10. The output shaft 32 is driven by the motor body 31 to rotate about a rotational axis (R). The output shaft 32 is rotatably retained on the outer surface of the tank 10, and is formed with an outer threaded surface 321.

In some embodiments, the slider 50 is retained slidably on the outer surface of the tank 10 along the rotational axis (R), and is formed with an inner threaded surface 51 configured to be in threaded engagement with the outer threaded surface 321 of the output shaft 32 so as to permit the slider 50 to be driven by the output shaft 32 to slide along the rotational axis (R) between a distal position, where the slider 50 is distal from the motor body 31, and a proximate position, where the slider 50 is proximate to the motor body 31.

In some embodiments, as shown in FIGS. 5 and 7, the actuating arm 40 is coupled to move with the slider 50, and includes a first horizontal portion 41, a vertical portion 42 and a second horizontal portion 43. The first horizontal portion 41 extends from the slider 50 over the end portion 13 of the tank 10 to terminate at an outer end 411. The vertical portion 42 extends downwardly from the outer end 411 of the first horizontal portion 41 to terminate at a lower end 421. The second horizontal portion 43 is coupled with the lower end 421 of the vertical portion 42 and extends toward the deformable membrane 20 to terminate at an inner end 431 such that when the actuating arm 40 is driven to move with the slider 50 from the first position (see FIG. 1) to the second position (see FIG. 2), the inner end 431 is moved to force the deformable membrane 20 to deform from the flat state to the deformed state.

In some embodiments, with reference to FIGS. 1, 2, 5 and 6, the deformable membrane 20 is deformed inwardly in the deformed state. In other words, in response to movement of the slider 50 from the distal position, toward the motor body 31, to the proximate position, the inner end 431 of the second horizontal portion 43 of the actuating arm 40 is brought into pressing engagement with the deformable membrane 20 so as to force the deformable membrane 20 to deform into the deformed state against a retaining force from the end portion 13 of the tank 10. In response to movement of the slider 50 from the proximate position, away from the motor body 31, to the distal position, the inner end 431 of the second horizontal portion 43 of the actuating arm 40 is brought to disengage from the deformable membrane 20 so as to permit the deformable membrane 20 to return back to the flat state by the retaining force, thereby allowing the communication port 102 to generate the predetermined pressure (e.g., a predetermined negative pressure).

In some other embodiments, with reference to FIGS. 3 to 6, the deformable membrane 20 is deformed outwardly in the deformed state. In this case, the inner end 431 of the second horizontal portion 43 of the actuating arm 40 is secured to the central portion of the deformable membrane 20. To be specific, in response to movement of the slider 50 from the proximate position, away from the motor body 31, to the distal position, the deformable membrane 20 is pulled by the inner end 431 of the second horizontal portion 43 of the actuating arm 40 so as to deform outwardly into the deformed state against the retaining force from the end portion 13 of the tank 10, thereby generating the predetermined pressure (e.g., a predetermined negative pressure) from the communication port 102. In response to movement of the slider 50 from the distal position, toward the motor body 31, to the proximate position, the inner end 431 of the second horizontal portion 43 of the actuating arm 40 is moved toward the opening 101 so as to permit the deformable membrane 20 to return back to the flat state by the retaining force.

In some embodiment, the pressure generating device 1 further includes a guiding mount 60 which is disposed on the end portion 13 of the tank 10, and which is formed with a guiding slot 61 configured to permit the first horizontal portion 41 to extend therethrough so as to guide movement of the first horizontal portion 41 when the actuating arm 40 is moved with the slider 50.

In some embodiment, the pressure generating device 1 further includes a retaining mount 70 mounted on the outer surface of the tank 10. The retaining mount 70 includes a base piece 71, a first piece 72 and a second piece 73. The base piece 71 is mounted on the outer surface of the tank 10, and is configured to permit the slider 50 to be slidably retained thereon. The first and second pieces 72, 73 are disposed proximate to and distal from the end portion 13 of the tank 10, and extend upwardly respectively from two ends of the base piece 71 so as to permit the slider 50 to slide between the first and second pieces 72, 73. In addition, the motor body 31 is mounted on the second piece 73, and the output shaft 32 extends through the second piece 73 and is rotatably supported by the first and second pieces 72, 73.

In some embodiment, the pressure generating device 1 further includes a photo sensor 80 which is disposed to be immovable relative to the tank 10 so as to detect a displacement of the slider 50.

In some embodiment, the pressure generating device 1 further includes a flag piece 90 which is mounted on and slidable with the slider 50, and which has a plurality of detectable positions for being detected by the photo sensor 80, thereby determining the displacement of the slider 50.

Figure 10:
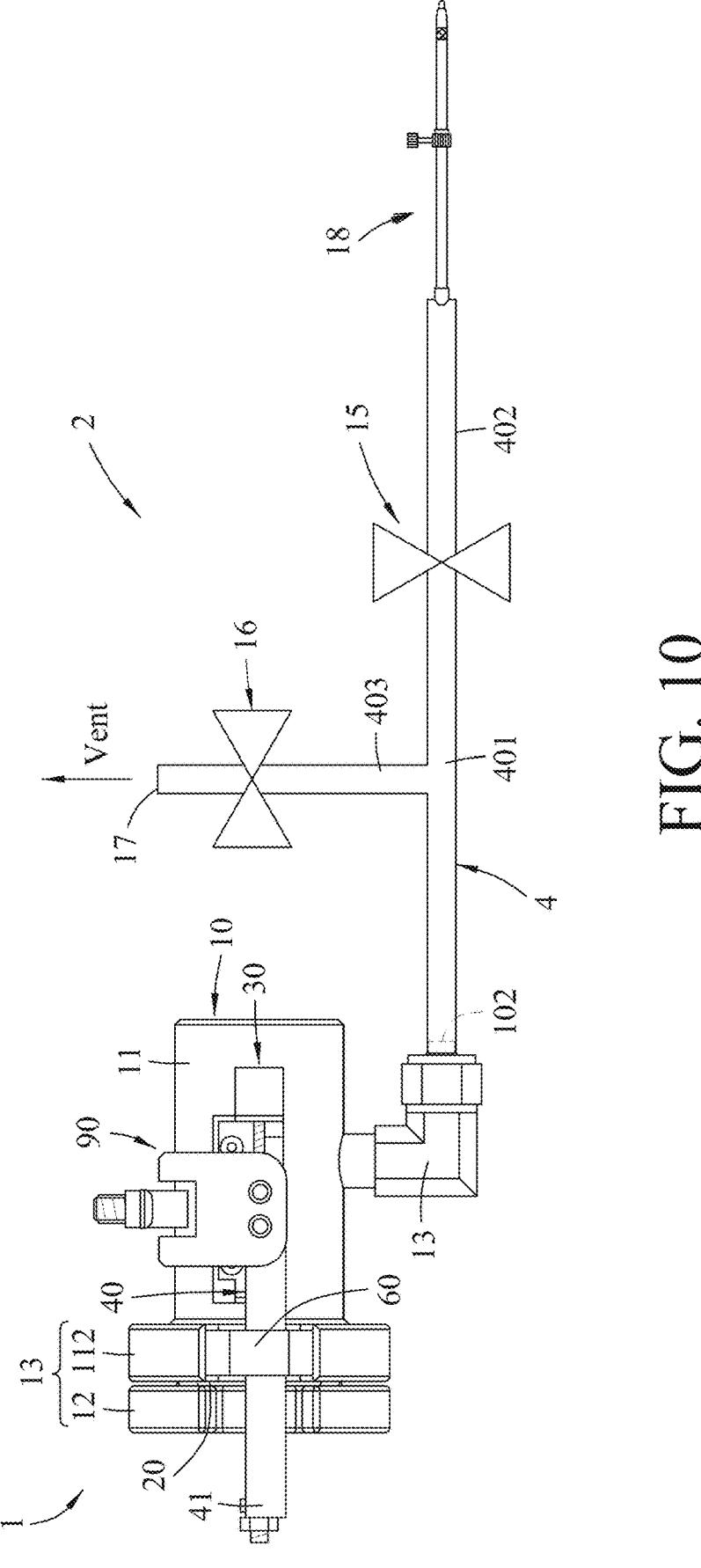
FIG. 10 is a perspective view illustrating a major part of a detecting system according to an embodiment of the disclosure.

FIG. 10 illustrates a major part of a detecting system 2 for detecting quality of the test sample (S) according to an embodiment of the disclosure. The detecting system 2 includes the pressure generating device 1, the micropipette 3 (see FIGS. 13 and 14) for sucking the test sample (S), and a connecting tube 4 disposed to connect the communication port 102 of the tank 10 to the micropipette 3 for applying the predetermined pressure (e.g., a predetermined negative pressure) from the pressure generating device 1 to the test sample (S).

In some embodiments, an inner diameter of the micropipette 3 ranges from about 10 microns to about 100 microns (e.g., about 40 microns to about 70 microns).

In some embodiments, by the pressure generating device 1, a pressure ranging from about 0.5 psi to about-0.5 psi is generated at a suction port 301 of the micropipette 3. For example, the pressure generated at the suction port 301 of the micropipette 3 may varied from about-0.03 psi to about-0.5 psi, from about 0.03 psi to about-0.5 psi, from about 0.03 psi to about 0.5 psi, or from about −0.03 psi to about 0.5 psi.

In some embodiments, referring to FIGS. 10, 11, 13 and 14, the detecting system 2 further includes a microscope 5 and an injection holder 18. The microscope 5 is used for monitoring the test sample (S) and the suction port 301 of the micropipette 3. To be specific, the test sample (S) is placed on a dish 501 of the microscope 5 and the injection holder 18 is connected between the connecting tube 4 and the micropipette 3. In operation, the suction port 301 of the micropipette 3 is retained by the injection holder 18 to be disposed on the dish 501 of the microscope 5, so as to facilitate the test sample (S) on the dish 501 to be retained and/or sucked by the suction port 301 of the micropipette 3.

In some embodiments, the connecting tube 4 includes a first tube segment 401 connected to the communication port 102 of the tank 10, and a second tube segment 402 connected to the micropipette 3 through the injection holder 18. The first and second tube segments 401, 402 are connected to each other through an adjusting valve 15 for adjusting the pressure generated at the suction port 301 of the micropipette 3. In some embodiments, the adjusting valve 15 is a solenoid valve.

In some embodiments, the detecting system 2 further includes a branch tube 403 which is connected to the first tube segment 401, and which has the venting port 17 opposite to the first tube segment 401. In addition, a venting valve 16 is coupled to the branch tube 403 to control a fluid communication between the chamber 100 and the venting port 17. To be specific, when the venting valve 16 is opened, the venting port 17 is in fluid communication with the chamber 100, and when the venting valve 16 is fully closed, the venting port 17 is prevented from being in fluid communication with the chamber 100. Therefore, when the venting valve 16 is opened, the pressure inside the chamber 100 is permitted to return to an atmospheric pressure. In some embodiments, the venting valve 16 is a solenoid valve.

Figure 12:
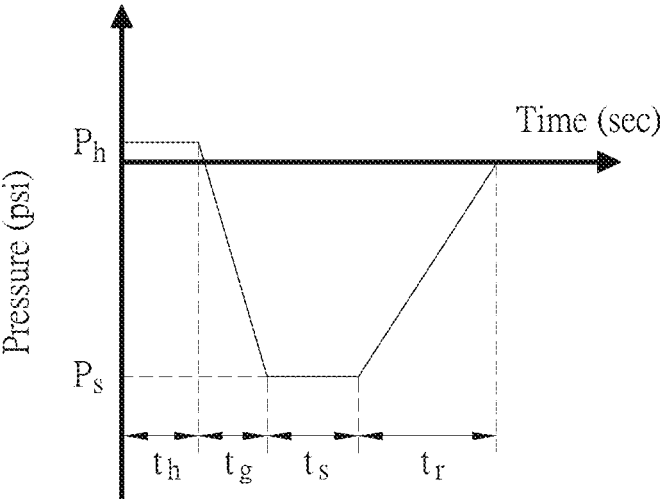
FIG. 12 is a graph illustrating a testing process for determining quality of a test sample in accordance with some embodiments.

FIG. 12 is a graph illustrating a testing process for determining the quality of the test sample (S) in accordance with some embodiments. The testing process shown in FIG. 12 is described with reference to FIGS. 10, 13 and 14. During the testing process illustrated in FIG. 12, the adjusting valve 15 is always opened.

Referring to FIGS. 10 and 12, in the beginning, the venting valve 16 is fully closed, and the pressure inside the chamber 100 is adjusted to and kept at an initial pressure (e.g., a slightly positive or negative pressure), and the position of the actuating arm 40 is also moved to permit the deformable membrane 20 to be kept at a home state. For example, in the case that the deformable membrane 20 is deformed inwardly (e.g., the embodiment shown in FIGS. 1 and 2), the home state of the deformable membrane 20 is the deformed state (see FIG. 2); while in the case that deformable membrane 20 is deformed outwardly (e.g., the embodiment shown in FIGS. 3 and 4), the home state of the deformable membrane 20 is the flat state (see FIG. 3). Due to the initial pressure of the chamber 100, as shown in FIG. 12, a slightly positive pressure ($P_h$) (e.g., about 0.01±10% psi) is generated at the suction port 301 of the micropipette 3 and kept for a time period ($t_h$), and thus the test sample (S) is retained by the suction port 301 of the micropipette 3 and is prevented from being sucked into the micropipette 3 (see FIG. 13). Then, by actuating the driving device 30 to cause transformation of the deformable membrane 20, a pressure from the communication port 102 is continuously reduced for a time period ($t_g$) (e.g., 2±10% seconds) so as to reach the predetermined pressure (e.g., a predetermined negative pressure), and meanwhile, a suction pressure generated at the suction port 301 of the micropipette 3 is gradually decreased to a stress pressure ($P_s$) (e.g., −0.1±10% psi). The stress pressure ($P_s$) lasts for a time period ($t_s$) (e.g., 1±10% second) and at this stage, as shown in a microscope image in FIG. 14, an aspiration depth (D) of the test sample (S) is determined using a computer program (not shown). Finally, the driving device 30 is further actuated to continuously increase the pressure inside the chamber 100 for a time period ($t_r$), thereby returning the deformable membrane 20 to the home state. Thereafter, the venting valve 16 is opened to permit the pressure inside the chamber 100 to return to the atmospheric pressure through the venting port 17. Please note that the pressure inside the chamber 100 is increased gradually so as to avoid blowing away the test sample (S) from the micropipette 3. In some other embodiments, before reduction to reach the stress pressure ($P_s$), the pressure ($P_h$) generated at the suction port 301 of the micropipette 3 may be kept at a slightly negative pressure (e.g., −0.01±10% psi) for a time period (e.g., 2±10% seconds) and for sticking the test sample (S).

During the testing process shown in FIG. 12, the slider 50 can be driven by the driving device 30 to move between the proximate and distal positions.

In some embodiments in which the deformable membrane 20 is deformed inwardly in the deformed state, (i) at the time period ($t_h$), the slider 50 is in the proximate position, the deformable membrane 20 is in the deformed state, and the actuating arm 40 is in the second position, and (ii) at the time period ($t_s$), the slider 50 is in the distal position, the deformable membrane 20 is in the flat state, and the actuating arm 40 is in the first position.

In some other embodiments in which the deformable membrane 20 is deformed outward in the deformed state, (i) at the time period ($t_h$), the slider 50 is in the proximate position, the deformable membrane 20 is in the flat state, and the actuating arm 40 is in the first position, and (ii) at the time period ($t_s$), the slider 50 is in the distal position, the deformable membrane 20 is in the deformed state, and the actuating arm 40 is in the second position.

Figure 15:
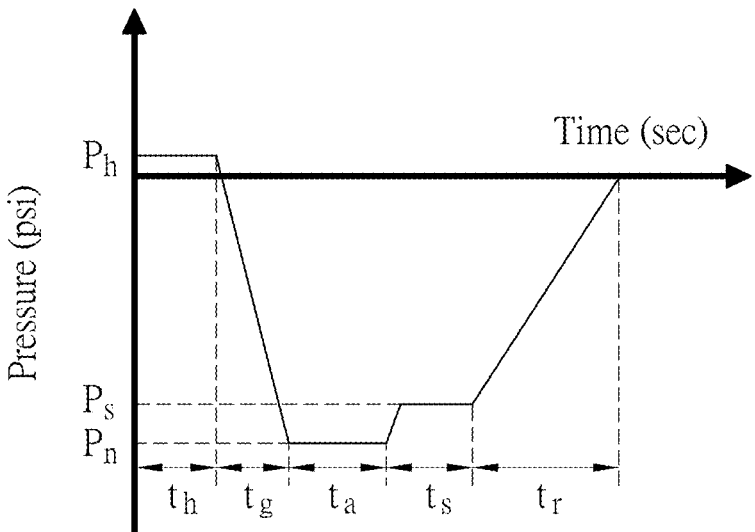
FIG. 15 is a graph illustrating another testing process for determining quality of a test sample in accordance with some embodiments.

FIG. 15 is a graph illustrating another testing process for determining the quality of the test sample (S) in accordance with some embodiments. The testing process shown in FIG. 15 is described with reference to FIGS. 10, 13 and 14. During the testing process illustrated in FIG. 15, the adjusting valve 15 is switched to adjust the pressure generated at the suction port 301 of the micropipette 3.

Referring to FIGS. 10 and 15, in the beginning, the venting valve 16 is fully closed, the adjusting valve 15 is fully closed, and the pressure inside the chamber 100 is adjusted to and kept at an initial pressure (e.g., a lower positive pressure), and the position of the actuating arm 40 is also moved to permit the deformable membrane 20 to be kept at a home state. For example, in the case that the deformable membrane 20 is deformed inwardly (e.g., the embodiment shown in FIGS. 1 and 2), the home state of the deformable membrane 20 is the deformed state (see FIG. 2); while in the case that the deformable membrane 20 is deformed outwardly (e.g., the embodiment shown in FIGS. 3 and 4), the home state of the deformable membrane 20 is the flat state (see FIG. 3). Due to the initial pressure of the chamber 100, by opening the adjusting valve 15, a slightly positive pressure ($P_h$) (e.g., about 0.01±10% psi) is generated at the suction port 301 of the micropipette 3 and kept for a time period ($t_h$) (see FIG. 15), and thus the test sample (S) is retained by the suction port 301 of the micropipette 3 and is prevented from being sucked into the micropipette 3 (see FIG. 13). Then, the adjusting valve 15 is closed, and by actuating the driving device 30 to cause transformation of the deformable membrane 20, a pressure inside the chamber 100 is continuously reduced for a time period ($t_g$) (e.g., 3±10% seconds) so as to reach a preset suction pressure ($P_n$) (e.g., −0.13±10% psi). The preset suction pressure ($P_n$) is kept for a time period ($t_a$) (e.g., 2±10% seconds). Then, during a time period ($t_s$) (e.g., 4±10% second), by slightly or fully opening the adjusting valve 15, the pressure inside the chamber 100 is slightly increased to and kept at a stress pressure ($P_s$) (e.g., −0.1±10% psi) and in meanwhile, the suction pressure generated at the suction port 301 of the micropipette 3 is substantially equal to the stress pressure ($P_s$). At this stage (i.e., the test sample (S) under the stress pressure ($P_s$)), as shown in a microscope image in FIG. 14, an aspiration depth (D) of the test sample (S) is determined using the computer program (not shown). Finally, the driving device 30 is further actuated to continuously increase the pressure inside the chamber 100 for a time period ($t_r$), thereby returning the deformable membrane 20 to the home state. Thereafter, the venting valve 16 is opened to permit the pressure inside the chamber 100 to return to the atmospheric pressure through the venting port 17. Please note that the pressure inside the chamber 100 is increased gradually so as to avoid blowing away the test sample (S) from the micropipette 3. In some other embodiments, before reduction to reach the preset suction pressure ($P_n$), the pressure ($P_h$) generated at the suction port 301 of the micropipette 3 may be kept at a slightly negative pressure (e.g., −0.01±10% psi) for a time period (e.g., 2±10% seconds) and for sticking the test sample (S).

During the testing process shown in FIG. 15, the slider 50 can be driven by the driving device 30 to move between the proximate and distal positions.

In some embodiments in which the deformable membrane 20 is deformed inwardly in the deformed state, (i) at the time period ($t_h$), the slider 50 is in the proximate position, the deformable membrane 20 is in the deformed state, and the actuating arm 40 is in the second position, and (ii) at the time periods ($t_a$, $t_s$), the slider 50 is in the distal position, the deformable membrane 20 is in the flat state, and the actuating arm 40 is in the first position.

In some other embodiments in which the deformable membrane 20 is deformed outwardly in the deformed state, (i) at the time period ($t_h$), the slider 50 is in the proximate position, the deformable membrane 20 is in the flat state, and the actuating arm 40 is in the first position, and (ii) at the time periods ($t_a$, $t_s$), the slider 50 is in the distal position, the deformable membrane 20 is in the deformed state, and the actuating arm 40 is in the second position.

With the provision of the detecting system 2 including the pressure generating device 1, a suction pressure can be generated at the suction port 301 of the micropipette 3 for sucking the test sample (S). Based on the aspiration depth (D) of the test sample (S), the quality of the test sample (S) may be determined. For example, a test sample (S) with a relatively smaller aspiration depth (D) may have a better quality. In addition, because the suction pressure generated using the pressure generating device 1 is relatively small, the test sample (S) is less likely to be damaged during the testing process, and the qualified test sample (S) can be transferred back to the mother for establishing a successful pregnancy.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A pressure generating device, comprising:
a tank defining a chamber therein, and including an opening and a communication port each of which is in fluid communication with said chamber;
a deformable membrane which is disposed to seal said opening, and which is deformable between a flat state and a deformed state;
a driving device disposed on an outer surface of said tank;
and an actuating arm coupled to be driven by said driving device to move between a first position, where said deformable membrane is in the flat state, and a second position, where said deformable membrane is forced to be in the deformed state, such that a predetermined pressure is generated through said communication port when said actuating arm is driven from one of the first and second positions to the other one of the first and second positions;
wherein said tank includes an end portion in which said opening is formed;
said driving device is a motor including a motor body which is mounted on said outer surface of said tank, and an output shaft which is driven by said motor body to rotate about a rotational axis, said output shaft being rotatably retained on said outer surface of said tank, and being formed with an outer threaded surface;

said pressure generating device further comprises a slider which is retained slidably on said outer surface of said tank along the rotational axis, and which is formed with an inner threaded surface configured to be in threaded engagement with said outer threaded surface of said output shaft so as to permit said slider to be driven by said output shaft to slide along the rotational axis between a distal position, where said slider is distal from said motor body, and a proximate position, where said slider is proximate to said motor body;
and wherein said actuating arm is coupled to move with said slider, and includes a first horizontal portion extending from said slider over said end portion of said tank to terminate at an outer end, a vertical portion extending downwardly from said outer end of said first horizontal portion to terminate at a lower end, and a second horizontal portion coupled with said lower end of said vertical portion and extending toward said deformable membrane to terminate at an inner end such that when said actuating arm is driven to move with said slider from the first position to the second position, said inner end is moved to force said deformable membrane to deform from the flat state to the deformed state.

2. The pressure generating device as claimed in claim 1, wherein said deformable membrane is deformed inwardly in the deformed state.

3. The pressure generating device as claimed in claim 1, wherein said deformable membrane is deformed outwardly in the deformed state.

4. The pressure generating device as claimed in claim 1, wherein said tank includes
a surrounding wall defining said chamber therein, and extending along a longitudinal axis to terminate at a closed end and an enlarged end which is opposite to said closed end and which is formed with said opening,
a surrounding mount detachably mounted to said enlarged end such that said deformable membrane is secured between said enlarged end and said surrounding mount to thereby seal said opening and such that a central portion of said deformable membrane is exposed from said surrounding mount when said surrounding mount is mounted to said enlarged end, and
a connection stem including a first connection end which is connected to said surrounding wall, and a second connection end which is opposite to said first connection end, said second connection end defining said communication port which is in fluid communication with said chamber through said connection stem.

5. The pressure generating device as claimed in claim 1, further comprising a guiding mount which is disposed on said end portion of said tank, and which is formed with a guiding slot configured to permit said first horizontal portion to extend therethrough so as to guide movement of said first horizontal portion when said actuating arm is moved with said slider.

6. The pressure generating device as claimed in claim 1, further comprising a retaining mount which is mounted on said outer surface of said tank and which includes a base piece mounted on said outer surface of said tank, and configured to permit said slider to be slidably retained thereon, and a first piece and a second piece which are disposed proximate to and distal from said end portion of said tank, and which extend upwardly respectively from two ends of said base piece so as to permit said slider to slide between said first and second pieces, wherein said motor body is mounted on said second piece, and said output shaft extends through said second piece and is rotatably supported by said first and second pieces.

7. The pressure generating device as claimed in claim 1, further comprising a photo sensor which is immovable relative to said tank so as to detect a displacement of said slider.

8. The pressure generating device as claimed in claim 7, further comprising a flag piece which is mounted on and slidable with said slider, and which has a plurality of detectable positions for being detected by said photo sensor, thereby determining the displacement of said slider.

9. The pressure generating device as claimed in claim 1, wherein: said deformable membrane is retained in the flat state by said end portion of said tank; in response to movement of said slider from the distal position to the proximate position, said inner end of said second horizontal portion of said actuating arm is brought into pressing engagement with said deformable membrane so as to force said deformable membrane to deform into the deformed state against a retaining force from said end portion of said tank; and in response to movement of said slider from the proximate position to the distal position, said inner end of said second horizontal portion of said actuating arm is brought to disengage from said deformable membrane so as to permit said deformable membrane to return to the flat state by the retaining force, thereby allowing said communication port to generate the predetermined pressure.

10. The pressure generating device as claimed in claim 1, wherein: said deformable membrane is retained in the flat state by said end portion of said tank; said inner end of said second horizontal portion of said actuating arm is secured to said central portion of said deformable membrane; and in response to movement of said slider from the proximate position to the distal position, said deformable membrane is pulled by said inner end of said second horizontal portion of said actuating arm so as to deform outwardly into the deformed state against a retaining force from said end portion of said tank, thereby allowing said communication port to generate the predetermined pressure; and in response to movement of said slider from the distal position to the proximate position, said inner end of said second horizontal portion of said actuating arm is moved toward said opening so as to permit said deformable membrane to return to the flat state by the retaining force.

11. A detecting system for detecting quality of a test sample including an oocyte or an embryo, comprising:
    said pressure generating device as claimed in claim 1;
    a micropipette for sucking the test sample; and
    a connecting tube disposed to connect said communication port of said tank to said micropipette for applying the predetermined pressure to the test sample.

12. The detecting system as claimed in claim 11, wherein an inner diameter of said micropipette ranges from 10 microns to 100 microns.

13. The detecting system as claimed in claim 11, wherein a pressure ranging from 0.5 psi to −0.5 psi is generated at a suction port of the micropipette.

14. The detecting system as claimed in claim 13, wherein the connecting tube includes a first tube segment connected to the communication port of the tank, and a second tube segment connected to the micropipette, said first and second tube segments being connected to each other through an adjusting valve for adjusting the pressure generated at said suction port of the micropipette.

* * * * *